United States Patent
Clementi et al.

(10) Patent No.: US 6,267,755 B1
(45) Date of Patent: Jul. 31, 2001

(54) METHOD OF HAIR DEPILATION

(75) Inventors: Gabriele Clementi; Gian Franco Bernabei; Mauro Galli, all of Florence (IT)

(73) Assignee: M & E Corporation of Delaware, Washington, DC (US)

( * ) Notice: Subject to any disclaimer, the term of this patent is extended or adjusted under 35 U.S.C. 154(b) by 0 days.

(21) Appl. No.: 09/335,698

(22) Filed: Jun. 18, 1999

Related U.S. Application Data

(60) Provisional application No. 60/133,844, filed on May 12, 1999, and provisional application No. 60/103,534, filed on Oct. 8, 1998.

(51) Int. Cl.[7] .................................................. A61B 18/18
(52) U.S. Cl. ................... 606/9; 606/11; 128/848
(58) Field of Search ........................... 606/9–19; 607/89; 128/898

(56) References Cited

U.S. PATENT DOCUMENTS

| | | | |
|---|---|---|---|
| 4,388,924 | 6/1983 | Weissman et al. ................... 128/303 |
| 5,059,192 | 10/1991 | Zaias ........................................ 606/9 |
| 5,423,803 | 6/1995 | Tankovich et al. ....................... 606/9 |
| 5,735,844 | * 4/1998 | Anderson et al. ........................ 606/9 |
| 6,106,514 | * 8/2000 | O'Donnell, Jr. .......................... 606/9 |

* cited by examiner

*Primary Examiner*—Linda C. M. Dvorak
*Assistant Examiner*—R. Kearney
(74) *Attorney, Agent, or Firm*—Foley & Lardner

(57) ABSTRACT

A method of hair depilation using an Nd:YAG laser which causes local heating at the hair bulb due to the absorption of the oxyhemoglobin contained in the capillaries. The Nd:YAG laser operates at 1060 nanometers. Each pulse is a special pulse having a first portion and a second portion, where power output in the first portion is 20 times greater than power output in the second portion. That way, the first portion of each pulse is used to quickly heat up the tissue to a damaging temperature, and the second portion maintains that temperature to cause hair removal for the tissue.

6 Claims, 3 Drawing Sheets

US 6,267,755 B1

METHOD OF HAIR DEPILATION

This application claims benefit of Prov. Ser. No. 60/133,844 filed May 12, 1994 and Ser. No. 60/103,534 filed Oct. 8, 1998.

BACKGROUND OF THE INVENTION

1. Field of the Invention

The present invention relates to a method of hair depilation; in particular, the present invention relates to a method of hair depilation using an Nd:YAG laser which causes local heating at the hair bulb due to the absorption of the oxyhemoglobin contained in the capillaries. The treatment can be performed on a single hair or a group of hairs using the Nd:YAG laser.

2. Description of the Related Art

At present, various methods for hair depilation using coherent light sources, such as lasers, are available. In particular, U.S. Pat. No. 5,059,192 describes a method of depilation based on the absorption of heat by melanin present in the hair follicle. The heat is provided by a Q-switched ruby laser, operating at a wavelength of 694 nm. The subsequent heating is provided at a direction substantially vertical to the hair follicle opening. Due to the heat, the follicle is severely damaged, interrupting the normal vital cycle and therefore its re-growth.

U.S. Pat. No. 5,423,803 uses a contaminant applied to the skin of a patient as a means for absorption of laser impulses of high peak intensity and very short duration. This causes irreversible damage to the hair bulb. For this purpose, a Q-switched Nd:YAG laser with emission at 1.06 $\mu$m is used, exploiting the minimum absorption that both the skin and the melanin have at this wavelength. U.S. Pat. No. 4,388,924 discloses a method that focuses a beam of light to destroy the vascularized part of the follicle. The beam of light is directed at an angle with respect to the hair follicle opening such that the beam of light is directed at the hair root. The hair root is heated, thereby causing damage to the blood vessels in the hair root. This in turn causes damage to the hair, preventing its re-growth.

SUMMARY OF THE INVENTION

An object of the present invention is to obtain a methodology for hair depilation and prevention of re-growth of hairs by use of a laser, such as an Nd:YAG laser.

Another object of the present invention is to obtain the irreversible damage of the hair follicle without interacting preferentially with the melanin, and therefore without damaging the derma that is crossed by the laser radiation.

Another object of the present invention is to provide for hair depilation without the use of externally-supplied contaminants.

Another object of the present invention is to not use a beam of laser radiation that focalizes inside the derma, because the focalization in such an important area as the derma proves to be uncontrolled and can cause irritating side effects.

Another object of the present invention is to obtain depilation and prevention of hair re-growth on patients who correspond to high class phototypes and whose treatment shows considerable contra-indications with lasers that interact with melanin.

Another object of the present invention is to obtain a method of hair depilation involving treatment of a single hair or a group of hairs.

BRIEF DESCRIPTION OF THE DRAWINGS

The above-mentioned objects and advantages of the invention will become more fully apparent from the following detailed description when read in conjunction with the accompanying drawings, with like reference numerals indicating corresponding parts throughout, and wherein.

DETAILED DESCRIPTION OF THE PREFERRED EMBODIMENTS

The present invention provides a method of hair depilation and prevention of hair re-growth through the destruction of the hair follicle obtained with a laser, such as an Nd:YAG laser that is used in a first embodiment. The treatment safeguards the dermic tissue through the laser radiation in a particular range of wavelengths.

Since the present invention involves the use of a laser, it is appropriate to utilize the dose necessary for the hair depilation and re-growth prevention treatment, and no more.

Figure 1:
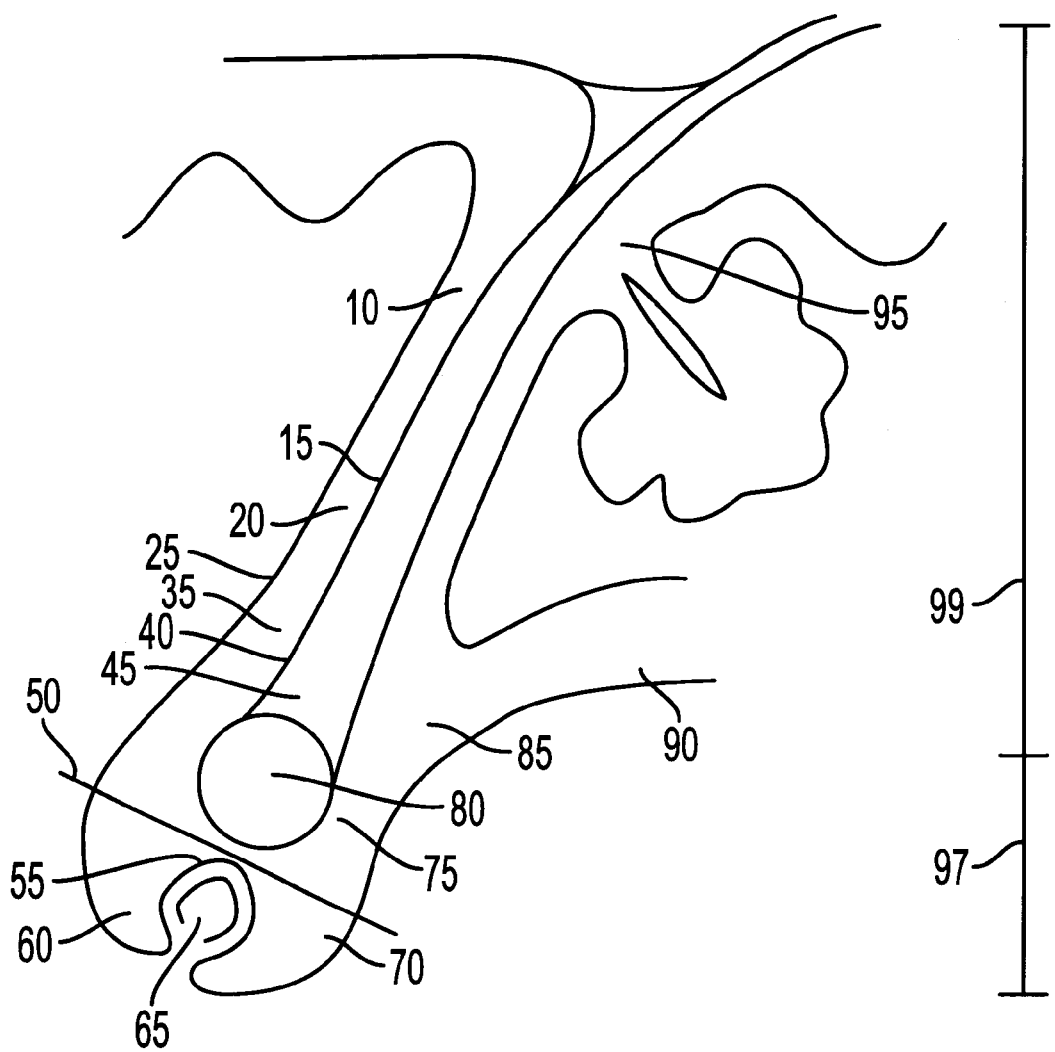
FIG. 1 is a diagram of a hair anatomy.
Figure 2:
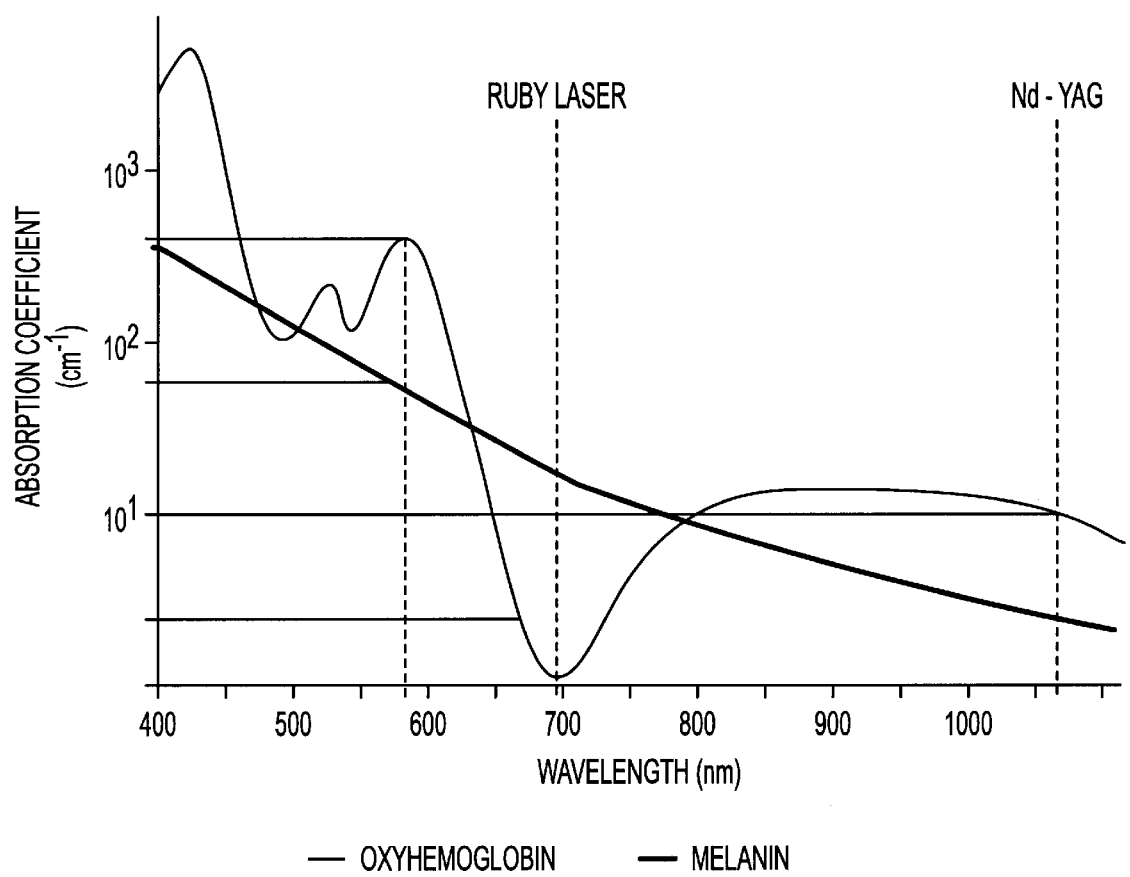
FIG. 2 is a diagram of showing the absorption of melanin and oxyhemoglobin over a range of wavelengths.

The hair follicle is an epithelial-connective structure responsible for the production of hair, as shown in FIG. 1. It occurs in the hair bulb that, when the hair is growing, the hair bulb has the shape of an upturned bowl with an epithelial component, so-called hair matrix, that covers a richly vascularized collagen area call the hair papilla.

As shown in FIG. 1, the hair follicle includes an outer root sheath 10, a Hemle's layer 15, a Huxley's layer 20 a first cuticle 25 (whereby elements 15, 20 and 25 are constitute an inner root sheath), a second cuticle 35, a cortex 40, a redulla 45 (where elements 35, 40, and 45 constitute a hair shaft), a critical line of auber 50, matrix cells 55, basement membrane 60, follicular papilla 65, hair bulb 70, lower follicle 75, keratogeneous zone 80, area of the bulge 85, arrector pilimuscle 90, and area of the searaceous gland 95. Also shown in FIG. 1 is a transient portion 97 of the hair follicle and a permanent portion 99 of the hair follicle.

By using a process of selective photo-thermolysis, the laser wavelength is selected to coincide with the maximum oxyhemoglobin absorption rate, contained in the vascularized region of the hair bulb. It is also selected such that it allows the lowest absorption possible, represented by the melanin in the derma affected.

This aspect is of fundamental importance because the hair follicles are deeply rooted in the derma (up to a few mm), and therefore a laser which will not damage the dermic tissue that is disposed between the laser and the hair follicles is recommended so as not to cause pain and/or skin damage to the patient.

Another important aspect of the present invention is the application of the method according to the first embodiment, to patients having a considerable amount of melanin present in their derma, either for reasons dealing with a race of a person (e.g., blacks have more melanin in their skin than Caucasians) or due to exposure to the sun. With some conventional hair depilation systems, such persons experience pain due to the laser treatment selecting melanin as the element to be heated to cause damage to the hair.

To reach such an aim, a first embodiment of the present invention preferably uses an Nd:YAG laser source with a wavelength of 1.06 $\mu$m, in order to obtain a deep and innocuous penetration in the skin, but with a dosage high enough to cause damage to the hair bulb due the effect of oxyhemoglobin absorption present in the hair bulb. By virtue of the first embodiment of the present invention, one obtains hair depilation and prevention of re-growth, while at the same time causes little damage to the melanin in the derma.

The dosage that is necessary to cause hair depilation and prevention of re-growth is 12J/cm$^2$ or higher, and the pulse length is 1 ms or higher.

A first method for treatment is described below. A laser beam is emitted through a fiber optic line, and it is conveyed to a handpiece providing, by a system of lenses, to shape a round spot of approximately 4 mm diameter at the point where it is to be used.

The handpiece is constructed so that it has a slightly divergent light beam. This is an important aspect of the first embodiment of the present invention, because focusing a laser beam in a non-homogeneous target, such as the derma, should be avoided since it is uncontrollable to a great extent.

When the laser radiation has a wavelength less than 1 μm, it undergoes a non-homogeneous scattering that tends to widen its diameter. This necessitates an external focalization in order to increase the fluence of the laser light. A purpose of the first embodiment of the present invention is to avoid an external focalization, which could result in a system that is somewhat uncontrollable.

The first embodiment of the present invention provides a therapeutic technique that irradiates the area around the hair opening on the surface (acrotrichio) with a single beam. In order to permit the operator to visualize the hair opening better, the skin of the patient is preferably shaved prior to performing the hair depilation method according to the present invention. In an alternative configuration, a water-based gel, which is transparent to the laser wavelength, is spread on the dermic surface so as to mark the areas already treated. The treatment continues by placing the laser beams alongside each other in particular dense areas or by hitting individual openings in the areas where there is less hair.

In yet another alternative configuration, there is pre-formed integrating in an automatic scanner in the handpiece in order to automatically arrange the laser spots, for example, in lines of three spots, which are squared out respectively with two and three spots at the sides. Such an alternative configuration permits one to rapidly treat areas which are particularly dense.

Hair types which are different due to either section or color may require energy dosage variations in order to obtain hair depilation and re-growth prevention.

While a first embodiment has been described herein, modification of the described embodiment may become apparent to those of ordinary skill in the art, following the teachings of the invention, without departing from the spirit and scope of the invention.

For example, the present invention accomplishes hair depilation and prevention of hair re-growth by applying laser energy at the entire portion of the hair that is below the skin. The wavelength of the radiation and the pulse widths are such that the melanin of the skin (and in the hair itself) is not affected very much, but where the oxy-hemoglobin (blood vessels) are affected by the radiation. The heat causes damage to the blood vessels themselves, both in the hair root and along the entire length of the hair that is below the surface of the skin, thereby causing damage to the hair. By attacking the blood vessels both in the hair root and in the shaft of the hair, in a manner using laser radiation that is not focused to just one spot (such as the hair bulb as in one of the conventional systems discussed previously) but rather to a particular range below the skin to be treated, and by using a wavelength of light that does not readily affect the melanin, the patient does not experience much pain, while the procedure is not limited to a focalizing required for certain conventional systems.

In the first embodiment, the pulses of radiation are provided to a patient's skin at pulse lengths from 1 to 40 mseconds, where the pulses of radiation are emitted by a laser source with wavelengths ranging from 1000 to 1500 nanometers, and where the pulses of radiation are emitted within a range of wavelengths that result in a low range of melanin absorption.

Also, the present invention involves providing laser light at such a range of wavelengths such that volumetric heating of blood vessels occurs. Studies indicate that the blood vessels in the hair bulb and in the hair shaft have a different size than blood vessels in the portions of the hand adjacent to the skin. Based on this size difference, the laser radiation can be optimized so that only the particular-sized blood vessels in the hair itself are affected by the heat provided by the laser radiation, thereby causing damage to those blood vessels and not to the other blood vessels in the hand that the laser radiation crosses on its way to the hair.

Figure 3:
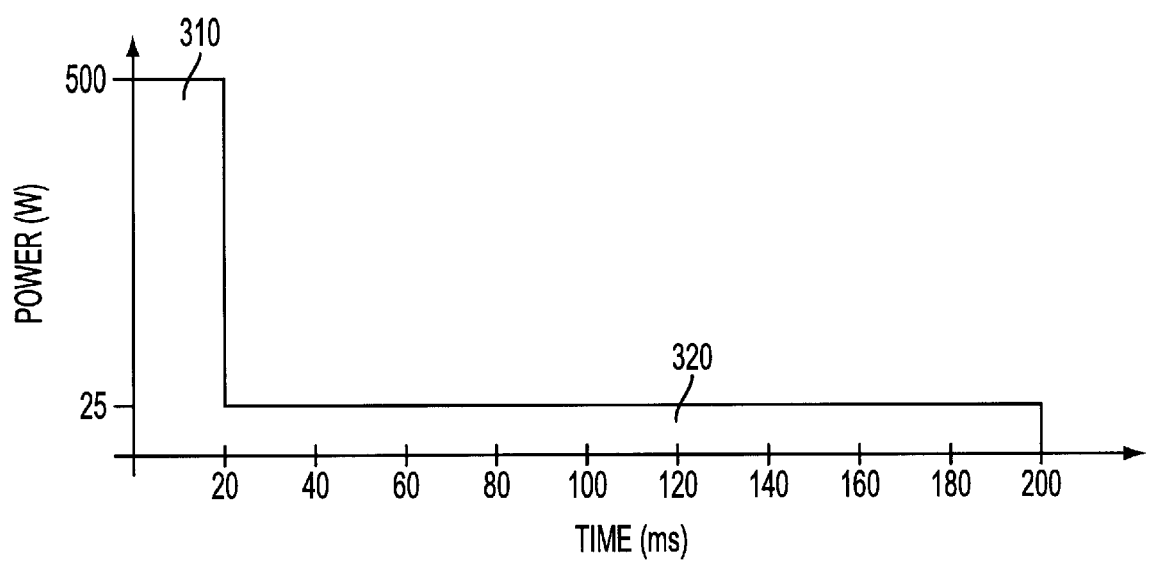
FIG. 3 is a diagram showing a special pulse according to a second embodiment of the invention.

A second embodiment of the present invention is described hereinbelow. The second embodiment utilizes a special shaped pulse, with that pulse preferably having 70% of its energy released in the first 10% of the pulse length, and having the remaining 30% of its energy released over the remaining 90% of its pulse length. Such a special pulse is shown in FIG. 3, with the first portion designated by label 310 and the second portion designated by label 320. The pulse is 200 msec long.

Higher energy in the first 10% of the pulse length is provided in the second embodiment in order to heat in a short amount of time the absorbing area of the tissue up to a temperature needed for starting the damaging effect to the hair follices, taking into consideration the thermal inertia. Such a temperature is typically within a range of from 60° C. to 80° C. In the remaining part of the pulse, the energy is released in order to hold such a temperature in order to complete the damaging effect, and such energy is preferably equal to the heat energy that is dissipated by thermal conduction by the absorbing area toward the surrounding tissue.

One type of pulse shape that follows such a criteria has a power ratio of 20 times between the first 10% of pulse length and the remaining 90% of pulse length. For example, the power output during the first portion of the pulse can be set to 500 Watts, and the power output during the second portion of the pulse can be set to 25 Watts.

In the second embodiment, the total energy during the first portion of the special pulse is 6 Joules, and the total energy output during the second portion of the special pulse is 2.7 Joules. A rectangular pulse of the same total energy will reach the damaging temperature only at the end of the pulse due to the fact that the temperature rise is linear for the rectangular pulse. Instead, by using a special pulse according to the second embodiment, the damaging temperature will be reached within the first 10% of the pulse length, and this temperature will remain substantially the same for the remaining time of the pulse. Such a special shaped pulse has the advantage, against a pure rectangular pulse of the same length, to have a better damaging effect without drawbacks of thermal damaging to the surround tissue that is not be to treated for hair removal. This reduces skin erithema (e.g., skin irritation and skin reddening), and it also reduces pain to the patient during hair removal treatment.

The preferred timing of such a special pulse is between 100 msec and 500 msec. While the special pulse has been described having 70% of its energy in the first 10% of the pulse length, and having the remaining 30% of its energy in the remaining 90% of the pulse length, other configurations of a special pulse are possible. The only criteria is that the first part of the pulse must be of sufficient energy to heat up the absorbing area of skin tissue to a desired temperature in a short period of time, and the second part of the pulse must be of sufficient energy to maintain that desired temperature to complete the damaging effect on hair follicles.

For example, a range of from 20 to 90% of the total energy can be provided in a first portion of a special pulse, where that first portion ranges from 2% to 20% of the total pulse length. Such a range of total energy and pulse length are within the scope of the second embodiment of the present invention as described above. For example, FIG. 3 shows a special pulse that has a first portion of 20 mseconds in duration, with a constant power of 500 watts in that first portion. FIG. 3 also shows that the special pulse has a second portion of 180 mseconds in duration, contiguous with the first portion, with a constant power of 25 watts in that second portion. Thus, the energy output in the first portion is 20 times greater than the energy output in the second portion of the special pulse. Also, please note that the first portion corresponds to 10% of the pulselength of the special pulse, and has 500 W * 20 mseconds=10000 Wmsec of output energy, while the second portion corresponds to 90% of the pulselength of the special pulse, and has 25 W * 180 mseconds=4500 Wmsec of output energy. Thus, the first portion, even though it is of less time duration than the second portion, provides more total energy output than the second portion. Also, the special pulse of the second embodiment may be used in the ranges specified in the first embodiment, or at other wavelengths known to cause hair removal.

What is claimed is:

1. A method of hair depilation and prevention of hair regrowth, comprising:

applying pulses of radiation to a skin of a patient, at a pulse length of from 100 to 500 msec, the pulses of radiation being emitted by a laser source with a wavelength ranging from 500 to 1500 nm and having a distribution of energy such that each pulse includes a first portion and a second portion, wherein the first portion of said each pulse comprises less than 20% of the pulse length has more than 20% of a total energy of said each pulse.

2. The method according to claim 1, wherein an energy output during the first portion of said each pulse is 20 times more than an energy output during the second portion of said each pulse.

3. The method according to claim 1, wherein a density on a skin of a patient is between 10 to 40 $J/cm^2$.

4. The method according to claim 1, wherein the wavelength corresponds to 1060 nanometers.

5. The method according to claim 1, wherein the first portion and the second portion of said each pulse are contiguous in time, and wherein the first portion of said each pulse is provided with a higher energy output than the second portion of said each pulse in order to heat up a predetermined portion of the skin of the patient to at least a fixed temperature within a fixed amount of time in order to provide a damaging effect on hair follicles on the predetermined portion of the skin of the patient, and wherein the second portion of said each pulse is provided with a lower energy output than the first portion of said each pulse in order to substantially hold a heated temperature of the predetermined portion of the skin of the patient, to compensate for heat energy that is dissipated by thermal conduction of the predetermined portion of the skin of the patient to other portions of the skin of the patient that are adjacent to the predetermined portion.

6. The method according to claim 5, wherein the fixed temperature is a temperature of between 60 to 80 degrees Celsius, and wherein the first amount of time is a time range of between 2 and 20 milliseconds.

* * * * *